United States Patent [19]

Andrews et al.

[11] Patent Number: 5,036,069
[45] Date of Patent: Jul. 30, 1991

[54] ANTHELMINTIC ACTIVE COMPOUND COMBINATIONS

[75] Inventors: Peter Andrews; Hubert Dorn, both of Wuppertal; Herbert Voege, Leverkusen, all of Fed. Rep. of Germany

[73] Assignee: Bayer Aktiengesellschaft, Leverkusen, Fed. Rep. of Germany

[21] Appl. No.: 420,784

[22] Filed: Oct. 12, 1989

Related U.S. Application Data

[63] Continuation of Ser. No. 153,620, Feb. 8, 1988, abandoned.

[30] Foreign Application Priority Data

Feb. 19, 1987 [DE] Fed. Rep. of Germany ....... 3705227

[51] Int. Cl.[5] ............................................. A01N 43/60
[52] U.S. Cl. ................................................... 514/249
[58] Field of Search .......................................... 514/249

[56] References Cited

U.S. PATENT DOCUMENTS

| | | | |
|---|---|---|---|
| 3,502,661 | 3/1970 | Kasubick et al. | 260/240 |
| 3,993,682 | 11/1976 | Kolling et al. | 260/470 |
| 3,996,368 | 12/1976 | Loewe et al. | 424/273 |

OTHER PUBLICATIONS

Nematocidal and Cesticidal Efficacy of a Tablet Formulation Containing Febantel, Pyrantel Embonate and Praziquantel in Dogs by: T. J. Hopkins, P. Gyr and P. M. Hedemann, Vet. Med. Rev., 59, pp. 71-75, 1988.
A Study of the Effectiveness of Mebendazole and Pyrantel Pamoate as a Combination Anthelmintic in Papua New Guinean children, Jeffifer Shield, Papua New Guinea Medical Journal, pp. 41-44, 1985.
A Comparative Study of Pyrantl Pamoate and a Combination of Mebendazole and Pyrantel Pamoate in the Treatment of Soil-Transmitted Helminths in a Rural Area, Indonesia, Purnomo and Partono, Southeast Asian Journal of Tropical Medicine and Public Health, Jun. 1981, vol. 12, No. 2, pp. 236-241.

Primary Examiner—Frederick E. Waddell
Assistant Examiner—Kevin E. Weddington
Attorney, Agent, or Firm—Sprung Horn Kramer & Woods

[57] ABSTRACT

An anthelminthic composition comprising a mixture of phenyl-guanidines of the formula

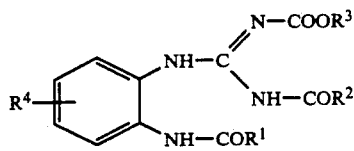

in which
R[1] represents hydrogen, optionally substituted alkyl, cycloalkyl, alkoxy, aryl or amino,
R[2] represents hydrogen, optionally substituted alkyl, cycloalkyl, alkenyl, alkinyl, aryl, alkoxy or alkenoxy,
R[3] represents hydrogen, optionally substituted alkyl, cycloalkyl, alkenyl, alkinyl or aryl,
R[4] represents alkyl, alkoxy, phenoxy, alkylthio, phenylthio, phenylsulphinyl, phenylsulphonyl or benzoyl which are in each case optionally substituted by halogen, alkoxy, alkylthio, halogenoalkoxy or halogenoalkylthio, or benzimidazoles of the formula

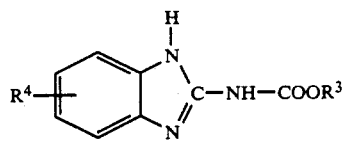

R[3] and R[4] have the meaning specified above together with tetrahydropyrimidines of the formula

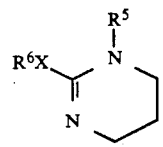

in which
R[5] represents hydrogen or alkyl, R[6] represents optionally substituted phenyl or thienyl, and X represents —$(CH_2)_{2-3}$— or —CH=CH—.

17 Claims, No Drawings

ANTHELMINTIC ACTIVE COMPOUND COMBINATIONS

This is a continuation of application Ser. No. 153,620, filed Feb. 8, 1988, now abandoned.

The present invention relates to the anthelamintic active compound combinations of phenylguanidines or benzimidazoles and tetrahydropyrimidines.

It has been disclosed that phenylguanidines and benzimidazoles are anthelmintically active against, for example, ascarids, hookworms and whipworms. However, their action against hookworms is not always completely satisfactory (U.S. Pat. Nos. 3,996,368 and 3,993,682).

It has been disclosed that tetrahydropyrimidines are anthelmintically active against, for example, ascarids and hookworms. However, the action against hookworms is again not always completely satisfactory in the case of these compounds (U.S. Pat. No. 3,502,661).

It has been disclosed that a combination of praziquantel (a hexahydropyrazinoisoquinoline) and pyrantel (a tetrahydropyrimidine) can be employed for combating tor americanus, a parasite of the small intestine in humans (Isr. J. Med. Sci 21 (1985) p. 710). Nothing is known on the use of this mixture in veterinary medicine.

It has been found that a combination of phenylguanidines of the formula I

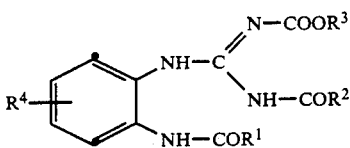

in which $R^1$ represents hydrogen, optionally substituted alkyl, cycloalkyl, alkoxy, aryl or amino, $R^2$ represents hydrogen, optionally substituted alkyl, tycloalkyl, alkenyl, alkinyl, aryl, alkoxy or alkenoxy, $R^3$ represents hydrogen, optionally substituted alkyl, cycloalkyl, alkenyl, alkinyl or aryl, $R^4$ represents alkyl, alkoxy, phenoxy, alkylthio, phenylthio, phenylsulphinyl, ohenylsulphonyl or benzoyl which are in each case optionally substituted by halogen, alkoxy, alkylthio, halogenoalkoxy or halogenoalkylthio, or benzimidazoles of the formula II

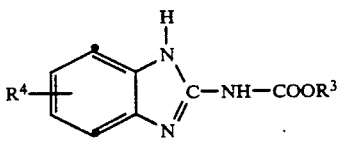

in which $R^3$ and $R^4$ have the meaning specified in the case of the compounds of the formula I, together with tetrahydropyrimidines of the formula III

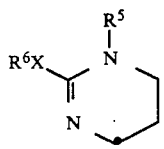

in which $R^5$ represents hydrogen or alkyl, $R^6$ represents optionally substituted phenyl or thienyl, and X represents $-(CH_2)_{2-3}-$ or $-CH=CH-$, is highly suitable for combating hookworms.

Moreover, the action of this combination extends beyond the sum of the action of the individual active compounds. The active compounds influence each other synergistically in the combination.

The phenylguanidines include, for example, febantel and netobimine.

The benzimidazoles include, for example, fenbendazole, albendazole, oxibendazole, ofendazole, mebendazole, flubendazole, parbendazole and luxabendazole.

The tetrahydropyrimidines include, for example, pyrantel, morantel and oxantel.

A mixture of febantel and pyrantel is particularly preferred.

The combinations according to the invention can contain other active compounds, for example against endoparasites. The following may be mentioned as such: anthelmintics from the class of the hexahydropyrazinoisoquinolines, such as, for example, praziquantel, or benazazepins, such as, for example, 2-cyclohexylcarbonyl-1,2,3,4,6, 7,8,12b-octahydropyrazino(2,1-a)(2)benzazepine-4-one, or salicylamides, such as, for example, niclosamide.

The active compounds are present in the combination in the following ratio:

phenylquanidine or benzimidazole to tetrahydropyrimidine as 1 to 1 up to 2 to 1.

The preparations are suitable for combating pathogenic endoparasites which occur in humans and in animal husbandry and animal breeding in productive, breeding, zoo, laboratory, experimental animals and pets, and have a favorable toxicity to warm-blooded animals. In this connection, they are active against all or individual stages of development of the pests and against resistant and normally sensitive species. By combating pathogenic endoparasites, it is intended that disease, cases of death and reduction in production (for example in the production of meat, milk, wool, hides, eggs, etc.) are reduced so that more economic and simpler animal husbandry is possible by means of the use of the active compounds. The pathogenic endoparasites include cestodes, trematodes, nematodes, acanthocephala, in particular:

From the order of the Pseudophyllides, for example: Diphyllobothrium spp., Spirometra spp., Schistocephalus spp., Ligula spp., Bothridium spp. and Diplogonoporus spp..

From the order of the Cyclophyllidea, for example: Mesocestoides spp, Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp. and Diplopylidium spp..

From the subclass of the Monogenea, for example: Gyrodactylus spp., Dactylogyrus spp. and Polystoma spp..

From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis.spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp. and Metagonimus spp:.

From the order of the Enoplida, for example: Trichuris spp., Capillaria spp., Trichomosoides spp. and Trichinella spp.:

From the order of the Rhabditia, for example: Micronema spp. and Strongyloides spp..

From the order of the Strongylida, for example: Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum· spp and Ollulanus spp.

From the order of the Oxyurida, for example: Oxyuris spp., Enterobius spp., Passalurus spp., Syphacia spp., Aspiculurls spp and Heterakis spp..

From the order of the Ascaridia, for example: Ascaris spp., Toxascaris spp.; Toxocara spp., Parascaris spp., Anisakis spp and Ascaridia spp..

From the order of the Spirurida, for example: Gnathostoma spp., Physaloptera spp., Thelazia spp., Gongylonema spp., Habronema spp., Parabronsma spp., Draschia spp. and Dracunculus spp The productive and breeding animals include mammals, such as, for example, cattle, horses, sheep, pigs, goats, camels, water buffalo, donkeys, rabbits, fallow deer and reindeer, pelt animals, such as, for example, mink, chinchilla and raccoons, birds, such as, for example, chickens, geese, turkeys and ducks, fresh and saltwater fish, such as, for example, trout, carp and eels, and reptiles.

The laboratory and experimental animals include mice, rats, guinea pigs, golden hamsters, dogs and cats.

The pets include dogs and cats.

The combination according to the invention is particularly preferably administered to dogs and cats.

Administration can take place both prophylactically and therapeutically.

The active compounds are administered, directly or in the form of suitable preparations, enterally, parenterally or dermally.

Enteral administration of the active compounds takes place, for example, orally in the form of powder, tablets, capsules, pastes, potions, granules, orally administered solutions, suspensions and emulsions, boli, medicated feed or drinking water.

Suitable preparations are:

oral solutions and concentrates for oral administration after dilution;

emulsions and suspension for oral administration; and semisolid preparations;

formulations in which the active compound is processed in an ointment base or in an oil-in-water or water-in-oil emulsion base;

solid preparations, such as powders, premixes or concentrates, granules, pellets, tablets, boli and capsules;

oral solutions are prepared by dissolving the active compound in a suitable solvent and, if appropriate, adding additives such as solubilizers, acids, bases, buffer salts, antioxidants and preservatives. The solutions are filtered and packed under sterile conditions.

The following may be mentioned as solvents: physiologically acceptable solvents, such as water, alcohQls, such as ethanol, butanol, benzyl alcohol, glycerol, propylene glycol and polyethylene glycol, N-methylpyrrolidone, and mixtures of the same The active compounds can, if appropriate, also be dissolved in physiologically acceptable vegetable or synthetic oils.

The following may be mentioned as solubilizers: solvents which promote dissolution of the active compound in the main solvent or substances which prevent precipitation of the active compound Examples are polyvinyl pyrrolidone, polyoxyethylated castor oil and polyoxyethylated sorbitan esters.

Preservatives are: benzyl alcohol, trichlorobutanol, p-hydroxybenzoic acid esters and n-butanol.

Oral solutions are administered directly. Concentrates are administered orally after prior dilution to the administration concentration.

Emulsions can be administered orally.

Emulsions are either of the water-in-oil type or of the oil-in-water type.

They are prepared by dissolving the active compound either in the hydrophobic phase or in the hydrophilic phase, and homogenizing this with the solvent of the other phase with the aid of suitable emulsifiers and, if appropriate, further auxiliaries, such as colorants, resorption-promoting substances, preservatives, antioxidants, light screens and viscosity-increasing substances.

The following may be mentioned as the hydrophobic phase (oils): paraffin oils, silicone oils, natural vegetable oils, such as sesame oil, almond oil and castor oil, synthetic triglycerides, such as capryl/capric acid biglyceride, a mixture of a triglyceride with vegetable fatty acids of chain length $C_{8-12}$ or with other specififatty cally selected natural fatty acids, partial glyceride mixtures of saturated or unsaturated, possibly also hydroxyl group-containing, fatty acids, and mono- and di- glycerides of $C_8/C_{10}$-fatty acids.

Fatty acid esters, such as ethyl stearate, di-nbutyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, capryl/capric acid esters of saturated fatty alcohols of chain length $C_{12}$–$C_{18}$, isopropyl stearate, oleyl oleate, decyl oleate, ethyl oleate, ethyl lactate, waxy fatty acid esters, such as synthetic duck urophygial gland fat, dibutyl phthalate, diisopropyl adipate and mixtures of esters related to the latter, inter alia.

Fatty alcohols, such as isotridecyl alcohol, 2-oclyldodecanol, cetylstearyl alcohol and oleyl alcohol.

Fatty acids, such as, for example, oleic acid, and mixtures thereof.

The following may be mentioned as the hydrophilic phase: water, alcohols, such as, for example, propylene glycol, glycerol and sorbitol, and mixtures thereof.

The following may be mentioned as emulsifiers: non-ionogenic surfactants, for example polyoxyethylated castor oil, polyoxyethylated sorbitan monooleate, sorbitan monostearate, glycerol monostearate, polyoxyethyl stearate and alkylphenol polyglycol ethers;

ampholytic surfactants, such as di-Na-N-lzuryl β-iminodipropionate or lecithin;

anionic surfactants, such as Na lauryl sulphate, fatty alcohol ether sulphates and the monoethanolamine salt of mono/dialkylpolyglycol ether orthophosphates;

cationic surfactants, such as cetyltrimethylammonium chloride.

The following may be mentioned as further auxiliaries: viscosity-increasing and emulsion-stabilizing substances, such as carboxymethyl cellulose, methyl cellulose and other cellulose and starch derivatives, polyacrylates, alginates, gelatin, gum arabic, polyvinyl pyrrolidone, polyvinyl alcohol, copolymers of methyl vinyl ether and maleic anhydride, polyethylene glycols, waxes, colloidal silica or mixtures of the substances mentioned.

Suspensions can be administered orally. They are prepared by suspending the active compound in an excipient liquid, if appropriate with addition of further auxiliaries, such as wetting agents, colorants, resorption-promoting substances, preservatives, antioxidants,-light screens.

Excipient liquids which may be mentioned are all homogeneous solvents and solvent mixtures.

Wetting agents (dispersants) which may be mentioned are the surfactants specified above.

Further auxiliaries which may be mentioned are those specified above.

Semisolid preparations can be administered orally. They differ from the suspensions and emulsions described above only in their higher viscosity.

In order to prepare to solid preparations, the active compound is mixed with suitable excipients, if appropriate with addition of auxiliaries, and converted to the form desired.

Excipients which may be mentioned are all physiologically acceptable inert solids. Inorganic and organic substances serve as such. Inorganic substances are, for example, common salt, carbonates. such as calcium carbonate, hydrogen carbonates, aluminum oxides, silicas, clays, precipitated or colloidal silicon dioxide and phosphates.

Organic substances are, for example, sugar, cellulose, nutrients and feedstuffs, such as milk powder, animal meals, ground and crushed cereal meals, and starches.

Auxiliaries are preservatives, antioxidants and colorants which have already been mentioned above.

Further suitable auxiliaries are lubricants, such as, for example, magnesium stearate, stearic acid, talcum and bentonites, disintegration-promoting substances, such as starch or transversely crosslinked polyvinyl pyrrolidone, binders, such as, for example, starch, gelatin or linear polyvinyl pyrrolidone, and dry binders, such as microcrystalline cellulose.

The combination according to the invention is particularly preferably administered in the form of tablets.

Preparations which are ready for administration contain the active compound in concentrations of 10 ppm -20 percent by weight, preferably 0.1-10 percent by weight.

Preparations which are diluted before administration contain the active compound in concentrations of 0.5-90 percent by weight, preferably 5 to 50 percent by weight.

In dogs and cats, the preferred administration concentration of the mixture according to the invention is 1-300 mg of tetrahydropyrimidine and 5-50 mg of phenylguanidine or benzimidazole per kg of live weight.

Particularly preferred concentrations employed per kg are 10-100 mg of tetrahydropyrimidine and 10-30 mg of phenylguanidine or benzimidazole.

Very particularly preferably, about 15 mg of tetrahydropyrimidine and about 15 mg or about 25 mg of phenylguanidine or benzimidazole respectively are employed per kg.

Further anthelmintic active compounds, such as, for example, praziquantel, can be added to the combination for administration at an administration rate of 0.1-20 mg, preferably 1-10 mg, particularly preferably about 5 mg, per kg.

EXAMPLE A

Action against Ancylostoms caninum in dogs.

Dogs infected experimentally with Ancylostoma caninum were treated after completion of the prepatency period of the parasites. The active compounds were administered orally as the pure active compound in gelatin capsules.

The degree of action was determined by counting the worms excreted with the droppings. The number of worms not killed and excreted by the treatment is then determined by dissecting the dogs. The following values were obtained here:

| Active compound | Dose mg/kg | Reduction of parasites in % |
|---|---|---|
| Febantel | 10 | 8 |
| Febantel | 25 | 40 |
| Pyrantel | 15 | 75 |
| Praziquantel | 5 | 0 |
| Febantel | 15 | |
| Pyrantel | 15 | 93 |
| Praziquantel | 5 | |
| Febantel | 25 | |
| Pyrantel | 15 | 95 |
| Praziquantel | 5 | |

EXAMPLE A

Action against Toxocara canis in dogs.

Dogs infected experimentally with Toxocara canis were treated after completion of the prepatency period the parasites. The active compounds were administered orally as the pure active compound in gelatin capsules.

The degree of action was determined by counting the worms excreted with the droppings. The number of worms not killed and excreted by the treatment is then determined by dissecting the dogs. The following values were obtained here:

| Active compound | Dose mg/kg | Reduction of parasites in % |
|---|---|---|
| Febantel | 10 | 47 |
| Febantel | 25 | 84 |
| Pyrantel | 15 | 75 |
| Praziquantel | 5 | 0 |

| Active compound | Dose mg/kg | Reduction of parasites in % |
| --- | --- | --- |
| Febantel | 15 | |
| Pyrantel | 15 | 94 |
| Praziquantel | 5 | |
| Febantel | 25 | |
| Pyrantel | 15 | 98 |
| Praziquantel | 5 | |

EXAMPLE 1

| Composition: | |
| --- | --- |
| Praziquantel active compound | 50.0 mg |
| Pyrantel active compound | 150.0 mg |
| Febantel active compound | 150.0 mg |
| Lactose | 100.0 mg |
| Maize starch | 143.0 mg |
| Sodium lauryl sulphate | 2.0 mg |
| Polyvinyl pyrrolidone | 18.0 mg |
| Microcrystalline cellulose | 49.0 mg |
| Colloidal silica | 1.0 mg |
| Magnesium stearate | 3.0 mg |

Preparation:
The active compounds are mixed in the ratio above with lactose and part of the corn starch and granulated in water with a solution of polyvinyl pyrrolidone and sodium lauryl sulphate, and the granules are dried. The dried granules are mixed with the other auxiliaries. The mixture, which is ready for tableting, is tableted into tablets weighing 660 mg, for example to a tablet size of diameter 13 mm.

EXAMPLE 2

| Composition: | |
| --- | --- |
| Pyrantel | 50 mg |
| Febantel | 250 mg |
| Colloidal silica | 10 mg |
| Microcrystalline cellulose | 600 mg |
| Whole milk powder | 2446 mg |

Preparation:
The substances are weighed out and mixed in the appropriate amount in the ratio above. The mixture is sieved and can be tableted directly in a tabletting machine into soft tablets of 3.5 g.

EXAMPLE 3

| Composition: | |
| --- | --- |
| Praziquantel | 1.43 g |
| Febantel | 7.15 g |
| Pyrantel embonate | 4.12 g |
| Wheat pollard | 87.30 g |

Preparation:
The substances are weighed out and mixed. Depending on the species and the weight of the animals, an appropriate part of this mixture is mixed with the feed —for example an amount of 3.5 g for a single treatment for a dog of 10 kg

EXAMPLE 4

Paste for oral administration or for mixing with the feed

| Composition: | |
| --- | --- |
| Praziquantel | 5.0 g |
| Pyrantel pamoate | 14.4 g |
| Febantel | 15.0 g |
| Sodium alginate | 1.0 g |
| Polysorbat 80 | 0.5 g |
| Methyl 4-hydroxybenzoate | 0.2 g |
| Demineralized water | 63.9 g |

Preparation:
Methyl 4-hydroxybenzoate is dissolved in hot water. After cooling, sodium alginate is dissolved in this solution, a gel forming. After addition of Polysorbat 80, the active compounds are suspended and homogenized in this gel. A paste is produced which can be administered directly orally or via the feed.

What is claimed is:

1. An anthelmintic composition for use in non-human animals, which comprises a synergistically effective amount against helminths of a combination of a phenylguanidine or benzimidazole compound selected from the group consisting of febantel, oxfendazole, fenbendazole, albendazole, luxbendazole, and flubendazole in admixture with a tetrahydropyrimidine compound which is pyrantel.

2. An anthelmintic composition according to claim 1, further comprising a benzimidazole selected from the group consisting of oxibendazole, mebendazole, and parbendazole.

3. A method for combating pathogenic endoparasites in non-human animals comprising administering to said animals an anthelmintically effective amount of a composition according to claim 2.

4. A composition according to claim 1, comprising further active compounds against helminths.

5. An anthelmintic composition for use in non-human animals, which comprises about 3-50 mg/kg of a compound selected from the group consisting of febantel, oxfendazole, fenbendazole, albendazole, luxbendazol, and flubendazol in admixture with about 3-50 mg/kg of pyrantel.

6. A method of combating helminths in non-human animals comprising administering to an animal in need of such treatment an anthelmintically effective amount of a composition according to claim 2.

7. An anthelmintic composition according to claim 1, wherein the ratio of tetrahydropyrimidine to phenylguanidine or benzimidazole is 1 to 1 up to 2 to 1.

8. A method for combating pathogenic endoparasites in non-human animals comprising administering to an animal in need of such treatment an anthelmintically effective amount of a composition according to claim 1.

9. A method according to claim 8, wherein the composition comprises a mixture of pyrantel and febantel.

10. A method according to claim 9, wherein the dosage administered is about 3-15 mg/kg of pyrantel and about 3-25 mg/kg of febantel.

11. A composition according to claim 1 useful for combating hookworms.

12. A composition according to claim 1, comprising a mixture of febantel and pyrantel.

13. A composition according to claim 1, comprising further active compounds against endoparasites.

14. A composition according to claim 2, wherein the ratio of the phenylguanidine and benzimidazole to the tetrahydropyrimidine is 1 to 1 up to 2 to 1.

15. A composition according to claim 2 comprising a mixture of febantel, pyrantel and praziquantel.

16. A method of combating helminths in non-human animals comprising administering to an animal in need of such treatment an anthelmintically effective amount of a composition according to claim 1.

17. A method according to claim 16 wherein the helminths combated are hookworms.

* * * * *